(12) United States Patent
Béjar Luque et al.

(10) Patent No.: US 10,856,551 B2
(45) Date of Patent: Dec. 8, 2020

(54) **USE OF *BACILLUS METHYLOTROPHICUS* AS A STIMULANT OF PLANT GROWTH AND BIOLOGICAL CONTROL MEANS, AND ISOLATES OF SAID SPECIES**

(71) Applicant: UNIVERSIDAD DE GRANADA, Granada (ES)

(72) Inventors: María Victoria Béjar Luque, Granada (ES); Inmaculada Llamas Company, Granada (ES); Cristina Ruíz García, Granada (ES); Emilia Quesada Arroquia, Granada (ES)

(73) Assignee: UNIVERSIDAD DE GRANADA, Granada (ES)

( * ) Notice: Subject to any disclaimer, the term of this patent is extended or adjusted under 35 U.S.C. 154(b) by 469 days.

(21) Appl. No.: 15/500,440

(22) PCT Filed: Jul. 31, 2015

(86) PCT No.: PCT/ES2015/070600
§ 371 (c)(1),
(2) Date: Jan. 30, 2017

(87) PCT Pub. No.: WO2016/016508
PCT Pub. Date: Feb. 4, 2016

(65) Prior Publication Data
US 2017/0215429 A1 Aug. 3, 2017

(30) Foreign Application Priority Data
Jul. 31, 2014 (ES) .................................. 201431158

(51) Int. Cl.
| A01N 63/00 | (2020.01) |
| A01N 63/10 | (2020.01) |
| C12N 1/20 | (2006.01) |
| C12R 1/07 | (2006.01) |

(52) U.S. Cl.
CPC ............ *A01N 63/00* (2013.01); *A01N 63/10* (2020.01); *C12N 1/20* (2013.01); *C12R 1/07* (2013.01)

(58) Field of Classification Search
None
See application file for complete search history.

(56) References Cited

U.S. PATENT DOCUMENTS

| 6,048,713 A | 4/2000 | Murakami et al. |
| 6,077,506 A | 6/2000 | Marrone et al. |
| 8,586,027 B2 | 11/2013 | Escobar Valdes et al. |
| 2008/0242543 A1 | 10/2008 | Banerjee et al. |
| 2010/0179060 A1 | 7/2010 | Fernandez Martinez et al. |
| 2014/0020136 A1 | 1/2014 | Van Der Wolf et al. |

FOREIGN PATENT DOCUMENTS

| CA | 2822178 A1 | 7/2012 | |
| CN | 102787084 A | 11/2012 | |
| CN | 103805534 A | 5/2014 | |
| EP | 0853671 A1 | 1/2005 | |
| KR | 20130096870 A | 9/2013 | |
| WO | 03/089640 A2 | 10/2003 | |
| WO | 2004/024865 A2 | 3/2004 | |
| WO | 2010/078708 A1 | 7/2010 | |
| WO | 2010/142055 A2 | 12/2010 | |
| WO | 2010/146204 A2 | 12/2010 | |
| WO | 2011/121408 A1 | 10/2011 | |
| WO | 2013/067275 A1 | 5/2013 | |
| WO | WO-2014175496 A1 * | 10/2014 | ............. A01N 63/02 |

OTHER PUBLICATIONS

EngMT-Zhou, D. et al. Bacillus methylotrophicus 4-L-16 for prevention and control of banana vascular wilt and its application. Chinese Patent Application Publication No. CN102787084(A); Date of Publication: Nov. 21, 2012, pp. 1-14. specif. pp. 1, 2, 4, 5, 7, 12.*
Burkett-Cadena et al. 2008. Suppressiveness of root-knot nematodes mediated by rhizobacteria. Biological Control 47: 55-59. specif. pp. 55,56, 57.*
Dunlap, C.A. et al. 2015. Phylogenomic analysis shows that *Bacillus amyloliquifaciens* subsp. plantarum is a later heterotypic synonym of Bacillus methylotrophicus. International Journal of Systematic and Evolutionary Microbiology 65: 2104-2109. specif. p. 210.*
International Search Report from corresponding International Patent Application No. PCT/ES2015/070600, dated Oct. 19, 2015.
Written Opinion from corresponding International Patent Application No. PCT/ES2015/070600, dated Oct. 19, 2015.
Ma Li et al.: "Phylogenetic diversity of bacterial endophytes of Panax notoginseng with antagonistic characteristics towards pathogens of root-rot disease complex", Antonie van Leeuwenhoek, Feb. 2013, vol. 103, No. 2, pp. 299-312.
Chunmei Du, "Research and application of Bacillus in agriculture", Chapter 2.2-2.3: pp. 81-88, Fleilongjiang University Press, 1st Edition (2013).

(Continued)

*Primary Examiner* — Renee Claytor
*Assistant Examiner* — Sharon M. Papciak
(74) *Attorney, Agent, or Firm* — Seed Intellectual Property Law Group LLP

(57) ABSTRACT

The invention relates to the use of microorganisms as plant growth stimulants and for the biological control of bacteria, insects, fungi and phytopathogenic nematodes. More specifically, the invention relates to the use of microorganisms of the genus *Bacillus*, more specifically the *Bacillus methylotrophicus* species, as well as to cultures thereof, compositions comprising these bacteria, different culture methods and the products comprising same, as plant growth stimulants and for the biological control of bacteria, insects, fungi and phytopathogenic nematodes.

11 Claims, 3 Drawing Sheets

Specification includes a Sequence Listing.

(56) References Cited

OTHER PUBLICATIONS

Office Action for Chinese Patent Application No. 201580045331.X, dated Nov. 22, 2018.
Pane et al., "Novel strains of Bacillus, isolated from compost and compost-amended soils, as biological control agents against soil-borne phytopathogenic fungi," *Biocontrol Science and Technology* 22(12):1373-1388, 2012.
Madhaiyan et al., "*Bacillus methylotrophicus* sp. Nov., a methanol-utilizing, plant-growth-promoting bacterium isolated from rice rhizosphere soil," *International Journal of Systematic and Evolutionary Microbiology* 60:2490-2495, 2010.
Shan et al., "Biocontrol of rice blast by the phenaminomethylacetic acid producer of *Bacillus methylotrophicus* strain BC79," *Crop protection* 44:29-37, 2013.
Khusro et al., "Strain Improvement of the New Strain of *Bacillus methylotrophicus* for Enhanced Production of Antimicrobial Metabolites," *PARIPEX—Indian Journal of Research* 2(11):243-244, 2013.

\* cited by examiner

SEQUENCE LISTING

```
<160> NUMBER OF SEQ ID NOS: 1

<210> SEQ ID NO 1
<211> LENGTH: 1502
<212> TYPE: DNA
<213> ORGANISM: Bacillus methylotrophicus, strain XT1

<400> SEQUENCE: 1
tgatcatggc tcaggacgaa cgctggcggc gtgcctaata catgcaagtc gagcggacag      60
atgggagctt gctccctgat gttagcggcg gacgggtgag taacacgtgg gtaacctgcc     120
tgtaagactg ggataactcc gggaaaccgg ggctaatacc ggatggttgt ttgaaccgca     180
tggttcaggc ataaaggtg gctttggcta ccacctacag atggacccgc ggcgcattag     240
ctagttggtg aggtaacggc tcaccaaggc gacgatgcgt agccgacctg agagggtgat     300
cggccacact gggactgaga cacggcccag actcctacgg gaggcagcag tagggaatct     360
tccgcaatgg acgaaagtct gacggagcaa cgccgcgtga gtgatgaagg ttttcggatc     420
gtaaagctct gttgttaggg aagaacaagt gccgttcaaa tagggcggca ccttgacggt     480
acctaaccag aaagccacgg ctaactacgt gccagcagcc gcggtaatac gtaggtggca     540
agcgttgtcc ggaattattg ggcgtaaagg gctcgcaggc ggtttcttaa gtctgatgtg     600 aaagccccg gctcaaccgg ggagggtcat tggaaactgg ggaacttgag tgcagaagag     660
gagagtggaa ttccacgtgt agcggtgaaa tgcgtagaga tgtggaggaa caccagtggc     720
gaaggcgact ctctggtctg taactgacgc tgaggagcga aagcgtgggg agcgaacagg     780
attagatacc ctggtagtcc acgccgtaaa cgatgagtgc taagtgttag ggggtttccg     840
ccccttagtg ctgcagctaa cgcattaagc actccgcctg gggagtacgg tcgcaagact     900
gaaactcaaa ggaattgacg ggggcccgca caagcggtgg agcatgtggt ttaattcgaa     960
gcaacgcgaa gaaccttacc aggtcttgac atcctctgac aatcctagag ataggacgtc    1020
cccttcgggg cagagtgac aggtggtgca tggttgtcgt cagctcgtgt cgtgagatgt    1080
tgggttaagt cccgcaacga gcgcaaccct tgatcttagt tgccagcatt cagttgggca    1140
```

-continued

```
ctctaaggtg actgccggtg acaaaccgga ggaaggtggg gatgacgtca aatcatcatg    1200 cccctttatga cctgggctac acacgtgcta caatggacag aacaaagggc agcgaaaccg    1260
cgaggttaag ccaatcccac aaatctgttc tcagttcgga tcgcagtctg caactcgact    1320
gcgtgaagct ggaatcgcta gtaatcgcgg atcagcatgc cgcggtgaat acgttcccgg    1380
gccttgtaca caccgcccgt cacaccacga gagtttgtaa cacccgaagt cggtgaggta    1440 acctttagg agccagccgc cgaaggtggg acagatgatt ggggtgaagt cctaacaagg    1500
ta                                                                   1502
```

USE OF *BACILLUS METHYLOTROPHICUS* AS A STIMULANT OF PLANT GROWTH AND BIOLOGICAL CONTROL MEANS, AND ISOLATES OF SAID SPECIES

This application is a National Stage Application of PCT/ES2015/070600, filed 31 Jul. 2015, which claims benefit of Serial No. P201431158, filed 31 Jul. 2014 in Spain and which applications are incorporated herein by reference. To the extent appropriate, a claim of priority is made to each of the above disclosed applications.

TECHNICAL FIELD OF THE PRESENT INVENTION

The main application of the present invention is in agriculture. The bacteria of the present invention, as well as the products produced by said bacteria, are useful as plant growth stimulants and for the control of plant pathogens such as bacteria, insects, fungi and nematodes.

PRIOR ART

1. Phytopathogenic Organisms

Phytopathogenic organisms are an important cause of diseases in plants; they determine changes in their shape, function or integrity and can lead to plant death. Nematodes, bacteria, insects, fungi and virus are included among such phytopathogenic organisms.

One of the most important groups are phytopathogenic fungi including, inter alia, species of the genera *Botrytis, Pythium, Alternaria, Fusarium, Phytophthora, Rhizoctonia, Colleotrichium, Eutypa, Rhizopus, Penicillium, Sclerotinia* and *Verticillium*. They cause local damage, such as leaf spots, tissue hypertrophy or smut, or widespread damage when they affect the root or vascular system, causing the plant to wilt and die. There are more than 8000 species that attack plants, some of which are very specific, and other of which have a wide range of hosts. The economic impact these organisms have is very important. By way of example, when *Botrytis cinnerea* affects vineyards, thousands of tons of wastage are produced in the wine-making industry.

Plant diseases caused by bacteria have a lower incidence than plant diseases caused by fungi or viruses (Vidhyasekaran 2002). Phytopathogenic bacteria include: *Erwinia amylovora*, responsible for the disease referred to as fire blight, particularly affecting pear trees, apple trees, medlar trees, quince trees and ornamental rosaceae; *Erwinia carotovora* (*Pectobacterium carotovorum*), soft rot producer; *Ralstonia solanacearum*, which causes rot and wilting in cultivated nightshades, but also in plants of more than fifty families; the different *Pseudomonas syringae* pathovars, which cause spots, burns and ulcerations;

*Agrobacterium tumefaciens*, a bacterium causing tumors in the collar, roots, and less often in stem and having a broad spectrum of guests, including more than 700 species; and *Xanthomonas campestris*, responsible for spots and burns in plants, inter alia.

Nematodes are also extremely important in agriculture. They are microscopic worms measuring between 0.2-1 mm with a stinger in the upper part they use to feed off the plant. The larvae enter through any part of the plant in contact with the moist soil, but primarily through the tip of the absorbent root hairs, because their stinger is not very strong. Once they are housed in the tissues, they neither move nor change from position. Symptoms present through the occurrence of typical nodules or thickening in the roots. This damage causes vessels to become obstructed and prevents absorption by the roots, which translates into less plant development and symptoms of wilting, chlorosis and stunting. Phytopathogenic nematodes include species of the genera *Meloidogyne, Heterodera, Radopholus* and *Pratylenchus*.

Insect pests are also an important problem in plants. In some cases they are bacterial and/or viral infection vectors. In other cases, they can weaken the plant and even cut off its growth and development, and controlling or eliminating insect pests is extremely complex. This is the case of borer beetles, which cut through the bark and get under it to build their tunnels and where the females lay eggs, or olive thrips, which suck the sap from the plant by eating buds, leaves, flowers, fruits and young shoots while at the same time injecting toxins into the plant, stopping the growth and deforming the affected organs. Another example is the whitefly, which absorb the sap until the leaves start to show yellow mottled spots and finally dry up. Furthermore, the secretions produced by this insect favor fungal proliferation. Aphids, leaf cutter ants, scale insects, sawflies, geranium bronzes, flower beetle, etc. are other examples of the main insects causing damage to plants.

2. Phytopathogen Control

To control the aforementioned the plant pathogens and increase crop yields, chemicals are generally used, these chemicals having a high associated toxicity in some cases, which negatively affects the environment. Both the water and the dirt are being contaminated; living beings that are fundamental for agriculture, such as pollinating insects, are being destroyed, and animal and human health are being affected. Directive 2009/128/EC of the European Parliament and of the Council, of 21 Oct. 2009, establishes the framework for action to achieve the sustainable use of said compounds and stresses priority areas for starting up ecologically sustainable innovative actions increasing agricultural productivity and resource efficiency.

An alternative to the indiscriminate use of chemicals in agriculture is the use of beneficial microorganisms, including both fungi and bacteria. It is a non-contaminating and environmentally-friendly method that considerably reduces the risks of pathogens becoming resistant.

2.1 Plant Growth-Promoting Rhizobacteria (PGPR)

Rhizobacteria are microorganisms in the soil living near the roots and they are also widely used in biocontrol. Since these bacteria are most often found in nature in the rhizosphere, they do not usually damage other beneficial organisms, and furthermore in many cases they benefit the ecosystem by stimulating plant growth and making agricultural production more sustainable. In turn, their effects on human health are minimal or nil. These microorganisms, also called plant growth-promoting rhizobacteria, or PGPR, colonize plant roots, compete with and control plant pathogens, and act as fertilizers.

PGPRs are characterized by their capacity to stimulate plant growth through direct or indirect mechanisms. Direct stimulation includes nitrogen fixation (Sessitsch et al., 2002); the production of hormones, such as auxins, gibberellins and cytokinins increasing the root elongation, division and size (Perrine et al., 2004; Garcia de Salamone et al., 2001); phosphate solubilization (Rodriguez and Fraga, 1999); and siderophore secretion (Carson et al., 2000), inter alia. The indirect plant growth stimulation includes various mechanisms relating to biocontrol of the phytopathogenic organisms (bacteria, fungi and nematodes, inter alia), which include: competition for ecological niches or substrates; production of hydrolytic enzymes (proteases, lipases, chitinases, collagenases and glucanases); the production of antibiotics (Hassan et al., 1997; Essalmani and Lahlou, 2003); root colonization, turning them into "biological casings" which delay nematode invasion (Rodriguez-Kábana 1997; Loeppler 1997); modification of root exudates, making them less appealing for nematodes (Oostendorp and Sikora, 1990); the production of siderophores and the production by some PGPRs of volatile compounds, such as acetoin and 2,3 butanediol, which cause an increase in plant resistance to infections (also called induced systemic resistance or ISR) (Choudhary and Johri 2009) and the production of $H_2S$ which prevents the development of nematodes (Mena 2004 and 2005).

Through all the described mechanisms, at given concentrations in the soil (at least $10^6$ microorganisms/ml are required) PGPRs act not only as plant growth stimulants (plant strengtheners or plant fertilizers), as biological control agents, preventing the development of phytopathogenic bacteria, fungi and nematodes.

Among the most widely used PGPR bacteria are the species of the genera Arthrobacter, Azospirillum, Bacillus, Pseudomonas, Rhizobium and Serratia, inter alia (Kloepper et al. 2004) Others such as Tsukamurelia paurometabola are also used, for example, in the bionematicide HeberNem®, effective in the control of Meloidogyne spp., Radopholus similis and Pratylenchus spp. Their mode of action is related to the release of hydrogen sulfide and chitinases (Mena, 2004 and 2005).

2.1.1. Bacteria of the Genus Bacillus

One of the most widely used bacteria in agriculture in the control of pathogens or as a PGPR are the bacteria of the genus Bacillus.

The bacteria from this genus have many of the aforementioned characteristics, and on the other hand spore formation provides for the long-term viability of this genus in commercial preparations, unlike other rhizobacteria such as Pseudomonas, Rhizobium or Serratia.

There are various commercial products of the genus Bacillus on the market. These include, inter alia:

| Product | Company | Composition | Control |
| --- | --- | --- | --- |
| Serenade ® | AgraQuest | B. subtilis QST713 | Fungi and bacteria in fruits |
| Ecoguard ® | Novozyme | B. licheniformis SB3088 | Sclerotinia homoeocarpa |
| Kodiak ® | Gustafson | B. subtilis GB03 | Fungi in cotton, soybean and legumes |
| Yield Shield ® | Gustafson | B. pumilus GB34 | Fungi in soybean |
| Bio Yield ® | Gustafson | B. amyloliquefaciens GB99 + B. subtilis GB122 | Fungi |
| Subtilex ® | Beker Underwood | B. subtilis MB1600 | Fungi in legumes, cotton and soybean |
| Hi Stick L + Subtilex ® | Beker Underwood | B. subtilis MB1600 + Rhizobium | Fungi in soybean |

Other patents/patent applications describing the use of microorganisms of the genus Bacillus for biological control are:

Strain of B. velezensis as a biofungicide (US 2010/0179060 A1)

Strain of B. pumilus as a nematicide (WO 2013/067275).

Strain of B. pumilus as an insecticide (WO2010146204).

Strain of B. thuringiensis as a nematicide (WO 2010/078708 A1, U.S. Pat. No. 6,077,506)

Strain of B. thuringiensis, its genes and toxins as a nematicide (EP 0853671).

Three strains of Bacillus subtilis, Pseudomonas putida and Sporobolomyces roseus for the control of phytopathogens (WO 2004/024865 A2).

Several strains of Bacillus spp. and Brevibacillus parabrevis with a fungicidal and bactericidal effect (WO 2010/142055).

Other bacteria used as PGPRs and in biological control are described in the following patents/patent applications:

Strain of Serratia for the control of pathogens (CA2822178 A1).

Three strains of Bacillus thuringiensis, Bacillus mojavensis and Azospirillum brasilense as plant growth stimulants and bionematicides (WO2011121408 A1).

A preparation containing different strains of Pseudomonas as a plant growth stimulant and as a biological control agent (U.S. Pat. No. 6,048,713 A).

A sulfur-oxidizing and plant growth promoting culture of Delftia acidovorans (US20080242543 A1).

Strains of Rhizobium to increase plant growth (WO2003089640 A2).

Shan et al. (Crop Protection 44 (2013), 29-37) describe use of Bacillus methylotrophicus strain BC79 in biocontrol of the disease in rice, also known as rice blast, caused by the fungus Magnaporthe oryzae.

Madhaiyan et al. (International Journal of Systematic and Evolutionary Microbiology (2010), 60, 2490-2495) describe Bacillus methylotrophicus sp., isolated from the rice rhizosphere.

Khusro et al. (Indian Journal of Research (2013) Vol. 2, Issue 11, pages 243-244) describe the improvement of a new Bacillus methylotrophicus strain for the increased production of antimicrobial metabolites.

Despite numerous attempts to develop plant growth stimulation strategies and/or strategies for the biological control of bacteria, fungi and/or phytopathogenic nematodes, there is pressing need today to develop alternative strategies or better strategies than those currently in place, which are capable of stimulating plant growth and/or biologically controlling the presence of phytopathogens, such as bacteria, fungi and/or nematodes, for example.

BRIEF DESCRIPTION OF THE INVENTION

The present invention relates to the use of microorganisms as plant growth stimulants and/or for the biological control of phytopathogenic bacteria, insects, fungi and/or nematodes. More specifically, the present invention relates to the use of microorganisms of the species Bacillus methylotrophicus, to different culture methods with respect to said microorganisms and to the products comprising them, as plant growth stimulants and/or for the biological control of phytopathogens such as bacteria, insects, fungi and/or nematodes. Preferably, the present invention relates to the use of microorganisms of the species Bacillus methylotrophicus, to different culture methods and to the products comprising them for the biological control of phytopathogens such as bacteria, insects, nematodes and phytopathogenic fungi.

In a particular embodiment, the present invention relates to the use of microorganisms of the species Bacillus methylotrophicus, to different culture methods with respect to said microorganisms and to the products comprising them, as plant growth stimulants and for the biological control of phytopathogens such as phytopathogenic bacteria, insects, fungi and nematodes. Preferably, the present invention relates to the use of microorganisms of the species *Bacillus methylotrophicus*, to different culture methods and to the products comprising them for the biological control of phytopathogenic bacteria, phytopathogenic nematodes, phytopathogenic insects and phytopathogenic fungi, with the exception of fungi belonging to the species *Magnaporthe oryzae*.

Preferably, the present invention relates to the use of microorganisms of the species *Bacillus methylotrophicus*, to different culture methods and to the products comprising them for the biological control of bacteria, such as those belonging to the species *Agrobacterium tumefaciens, Pectobacterium atrosepticum, Ralstonia solanacearum* and *Xanthomonas campestris*, for example; fungi, such as oidium, *Botrytis* or those belonging to the species *Alternaria alternata, Aspergillus niger, Botrytis cynerea, Fusarium oxysporum, Phytophthora cactorum, Phytophthora cinnamomi, Rhizopus oryzae, Sclerotinia sclerotiorum, Thanatephorus cucumeris* and *Verticillium dahliae*, for example; insects, such as the whitefly and aphid, for example; and/or nematodes such as the species belonging to the genera *Meloidogyne, Heterodera, Globodera, Pratylenchus, Paratylenchus, Ratylenchus, Xiphinema, Trichodorus*, for example, and generally all parasitic plant nematodes.

Another object of the present invention relates to microorganisms belonging to *Bacillus methylotrophicus* strain XT1 (deposit number CECT8661) deposited on 23 Apr. 2014 in the Colección Española de Cultivos Tipo (CECT—Spanish Type Culture Collection) by the Universidad de Granada and/or microorganisms with a high degree of homology with strain XT1, the 16S rRNA gene DNA sequence of which is identical by at least 99.6%, 99.7%, 99.8% or 99.9% to the 16S rRNA gene DNA sequence of strain XT1, based on the identity of all the nucleotides of said DNA sequences; and/or microorganisms belonging to *Bacillus methylotrophicus* strain XT2 (deposit number CECT8662) deposited on 23 Apr. 2014 in the Colección Española de Cultivos Tipo (CECT—Spanish Type Culture Collection) by the Universidad de Granada and/or microorganisms with a high degree of homology with strain XT2, the 16S rRNA gene DNA sequence of which is identical by at least 99.6%, 99.7%, 99.8% or 99.9% to the 16S rRNA gene DNA sequence of strain XT2, based on the identity of all the nucleotides of said DNA sequences.

Another object of the present invention is a bacteria culture comprising or consisting of microorganisms belonging to *Bacillus methylotrophicus* strain XT1 and/or microorganisms with a high degree of homology with strain XT1, the 16S rRNA gene DNA sequence of which is identical by at least 99.6%, 99.7%, 99.8% or 99.9% to the 16S rRNA gene DNA sequence of strain XT1, based on the identity of all the nucleotides of said DNA sequences; and/or microorganisms belonging to *Bacillus methylotrophicus* strain XT2 and/or microorganisms with a high degree of homology with strain XT2, the 16S rRNA gene DNA sequence of which is identical by at least 99.6%, 99.7%, 99.8% or 99.9% to the 16S rRNA gene DNA sequence of strain XT2, based on the identity of all the nucleotides of said DNA sequences.

A further object of the present invention relates to a composition comprising microorganisms belonging to *Bacillus methylotrophicus* strain XT1 and/or microorganisms with a high degree of homology with strain XT1, the 16S rRNA gene DNA sequence of which is identical by at least 99.6%, 99.7%, 99.8% or 99.9% to the 16S rRNA gene DNA sequence of strain XT1, based on the identity of all the nucleotides of said DNA sequences; and/or microorganisms belonging to *Bacillus methylotrophicus* strain XT2 and/or microorganisms with a high degree of homology with strain XT2, the 16S rRNA gene DNA sequence of which is identical by at least 99.6%, 99.7%, 99.8% or 99.9% to the 16S rRNA gene DNA sequence of strain XT2, based on the identity of all the nucleotides of said DNA sequences.

Another object of the present invention relates to the use of the bacteria, cultures and/or compositions described above in a method for stimulating plant growth and/or in a method for the biological control of phytopathogenic organisms.

More specifically, one object of the present invention is use of the bacteria belonging to strains XT1 or XT2 (or those microorganisms having a high degree of homology with these strains, as described above), the cultures or compositions thereof comprising them, as well as the products comprising one of them or the products that can be obtained from them or from the culture thereof as plant growth stimulants and/or for the biological control of plant pathogens, such as bacteria, insects, fungi and/or nematodes.

More specifically, one object of the present invention is use of the bacteria belonging to strains XT1 or XT2 (or those microorganisms having a high degree of homology with these strains, as described above), the cultures or compositions thereof comprising them, as well as the products comprising one of them or the products that can be obtained from them or from the culture thereof as plant growth stimulants and/or for the biological control of plant pathogens, such as fungi (with the exception of fungi belonging to the species *Magnaporthe oryzae*) and/or nematodes.

Preferably, the bacteria belonging to strains XT1 or XT2 (or those microorganisms having a high degree of homology with these strains), the cultures or compositions thereof comprising them, as well as the products comprising one of them or the products that can be obtained from them or from the culture thereof are used as plant growth stimulants and/or for the biological control of plant pathogens, selected from the list comprising or consisting of:

Bacteria belonging to the species *Agrobacterium tumefaciens, Pectobacterium atrosepticum, Ralstonia solanacearum* and *Xanthomonas campestris*, fungi belonging to the species *Alternaria alternata, Aspergillus niger, Botrytis cynerea, Fusarium oxysporum, Phytophthora cactorum Phytophthora cinnamomi, Rhizopus oryzae, Sclerotinia sclerotiorum, Thanatephorus cucumeris* and *Verticillium dahliae*; insects belonging to the family Aphididae, as well as insects belonging to the species commonly referred to as whitefly, and/or nematodes, such as those belonging to the genera *Meloidogyne, Heterodera, Globodera, Pratylenchus, Paratylenchus, Ratylenchus, Xiphinema* and/or *Trichodorus*, for example.

Preferably, the bacteria belonging to strains XT1 or XT2 (or those microorganisms having a high degree of homology with these strains, as described above), the cultures or compositions thereof comprising them, as well as the products comprising one of them or the products that can be obtained from them or from the culture thereof are used as plant growth stimulants and/or for the biological control of nematodes, preferably nematodes belonging to one of the following genera: *Meloidogyne, Heterodera, Globodera, Pratylenchus, Paratylenchus, Ratylenchus, Xiphinema* and/or *Trichodorus*.

Preferably, the bacteria belonging to strains XT1 or XT2 (or those microorganisms having a high degree of homology with these strains, as described above), the cultures or compositions thereof comprising them, as well as the products comprising one of them or the products that can be obtained from them or from the culture thereof are used as plant growth stimulants and/or for the biological control of *Agrobacterium tumefaciens, Pectobacterium atrosepticum, Ralstonia solanacearum* and *Xanthomonas campestris*.

Preferably, the bacteria belonging to strains XT1 or XT2 (or those microorganisms having a high degree of homology with these strains, as described above), the cultures or compositions thereof comprising them, as well as the products comprising one of them or the products that can be obtained from them or from the culture thereof are used as plant growth stimulants and/or for the biological control of fungi belonging to the species *Alternaria alternata, Aspergillus niger, Botrytis cynerea, Fusarium oxysporum, Phytophthora cactorum, Phytophthora cinnamomi, Rhizopus oryzae, Sclerotinia sclerotiorum, Thanatephorus cucumeris* and *Verticillium dahliae*, even more preferably for the biological control of *Botrytis cinnerea*.

Preferably, the bacteria belonging to strains XT1 or XT2 (or those microorganisms having a high degree of homology with these strains, as described above), the cultures or compositions thereof comprising them, as well as the products comprising one of them or the products that can be obtained from them or from the culture thereof are used as plant growth stimulants and/or for the biological control of insects belonging to the family Aphididae, as well as insects belonging to the species commonly referred to as "whitefly", more specifically, the species *Trialeurodes vaporariorum*, predominant in greenhouses.

Another object of the present invention relates to a method for stimulating plant growth comprising the steps of:
a. obtaining the bacteria, bacteria cultures or compositions as previously described; and
b. putting a plant in contact with the bacteria, bacteria cultures or compositions obtained in step a).

Another object of the present invention relates to a method for stimulating plant growth comprising the steps of:
a. obtaining the bacteria, bacteria cultures or compositions as previously described; and
b. putting a plant affected by a phytopathogen in contact with the bacteria, bacteria cultures or compositions obtained in step a).

Another object of the present invention relates to a method for the biological control of phytopathogenic organisms comprising the steps of:
a. obtaining the bacteria, bacteria cultures or compositions as previously described; and
b. putting a plant affected by a phytopathogen in contact with the bacteria, bacteria cultures or compositions obtained in step a).

Another object of the present invention relates to a method for the biological control of phytopathogenic fungi belonging to the species *Alternaria alternata, Aspergillus niger, Botrytis cynerea, Fusarium oxysporum, Phytophthora cactorum Phytophthora cinnamomi, Rhizopus oryzae, Sclerotinia sclerotiorum, Thanatephorus cucumeris* and *Verticillium dahliae*, preferably belonging to the species *Botrytis cinnerea*, comprising the steps of:
a. obtaining the bacteria, bacteria cultures or compositions as previously described; and
b. putting a plant affected by a phytopathogen in contact with the bacteria, bacteria cultures or compositions obtained in step a.

Another object of the present invention relates to a method for the biological control of phytopathogenic bacteria belonging to the species *Agrobacterium tumefaciens, Pectobacterium atrosepticum, Ralstonia solanacearum* and *Xanthomonas campestris* comprising the steps of:
a. obtaining the bacteria, bacteria cultures or compositions as previously described; and
b. putting a plant affected by a phytopathogen in contact with the bacteria, bacteria cultures or compositions obtained in step a.

One object of the present invention relates to a method for the biological control of phytopathogenic nematodes (such as for example *Meloidogyne, Heterodera, Globodera, Pratylenchus, Paratylenchus, Ratylenchus, Xiphinema* and/or *Trichodorus* species) comprising the steps of:
a. obtaining the bacteria, bacteria cultures or compositions as previously described; and
b. putting a plant affected by a phytopathogen in contact with the bacteria, bacteria cultures or compositions obtained in step a).

Another object of the present invention relates to a method for the biological control of phytopathogenic insects belonging to the family Aphididae, as well as insects belonging to the species commonly referred to as whitefly, comprising the steps of:
a. obtaining the bacteria, bacteria cultures or compositions as previously described; and
b. putting a plant affected by a phytopathogen in contact with the bacteria, bacteria cultures or compositions obtained in step a).

The methods described in the present invention can furthermore comprise the use of a system for distributing the bacteria, cultures or compositions of the present invention. For example, the methods of the present invention can comprise the use of drippers for distributing the bacteria, cultures or compositions of the present invention. For example, the methods of the present invention can comprise the use of self-compensating drippers for distributing the bacteria, cultures or compositions of the present invention. For example, the methods of the present invention can comprise the use of localized irrigation systems (such as microsprinklers with rotating or diffusing elements for example) for distributing the bacteria, cultures or compositions of the present invention. For example, the methods of the present invention can comprise the use of sprinklers for distributing the bacteria, cultures or compositions of the present invention.

In a preferred embodiment, the aforementioned methods use bacteria, bacteria cultures or compositions comprising *Bacillus methylotrophicus*, strains XT1 and/or XT2, deposited in the Colección Española de Cultivos Tipo (CECT—Spanish Type Culture Collection) with deposit number CECT8661 and CECT8662, respectively.

BRIEF DESCRIPTION OF THE DRAWINGS

In order to complement the description that is being made and to help improve understanding of the features characteristics of the invention according to several embodiments, the following drawings are shown herein with an illustrative and non-limiting character.

DETAILED DESCRIPTION OF THE INVENTION

Figure 1:
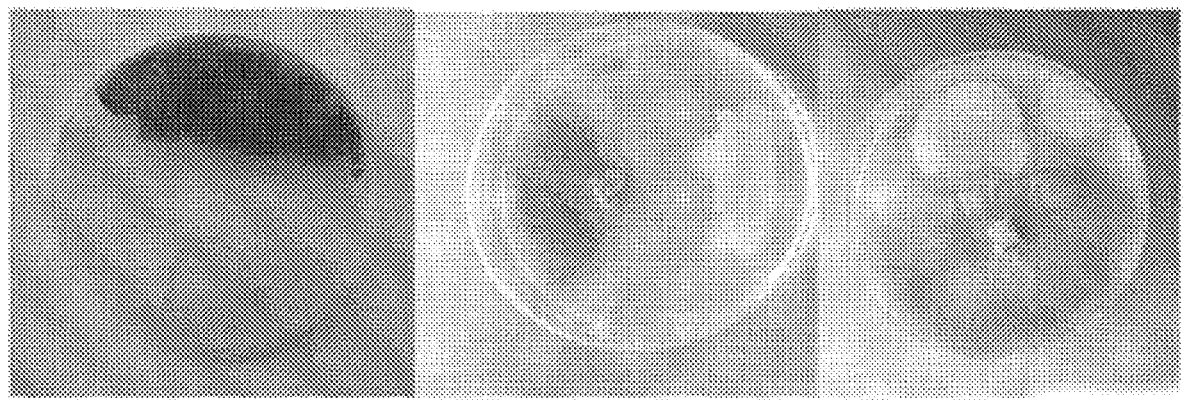
FIG. 1. Inhibition zone of XT1 and XT2 against *Botrytis* and inhibition zone of XT1 against *Fusarium*.

The present invention relates to the use of microorganisms as plant growth stimulants and for the biological control of phytopathogenic bacteria, insects, fungi and nematodes. More specifically, the present invention relates to the use of microorganisms of the genus *Bacillus*, specifically of the species *Bacillus methylotrophicus*, to cultures thereof, to compositions comprising these bacteria, to different culture methods and to the products comprising them, as plant growth stimulants and for the biological control of phytopathogenic bacteria, insects, fungi and nematodes. Preferably, the present invention relates to the use of microorganisms of the species *Bacillus methylotrophicus*, to cultures thereof, to compositions comprising these bacteria, to different culture methods and to the products comprising them for the biological control of bacteria, insects, phytopathogenic nematodes and fungi.

Preferably, the present invention relates to the use of microorganisms of the species *Bacillus methylotrophicus*, to cultures thereof, to compositions comprising these bacteria, to different culture methods and to the products comprising them for the biological control of bacteria, insects, phytopathogenic nematodes and fungi, with the exception of the fungi belonging to the species *Magnaporthe oryzae*.

Preferably, the present invention relates to the use of microorganisms of the species *Bacillus methylotrophicus*, to cultures thereof, to compositions comprising these bacteria, to different culture methods and to the products comprising them for the biological control of bacteria belonging to the species *Agrobacterium tumefaciens, Pectobacterium atrosepticum, Ralstonia solanacearum* and *Xanthomonas campestres*; fungi belonging to the species *Alternaria alternata, Aspergillus niger, Botrytis cynerea, Fusarium oxysporum, Phytophthora cactorum Phytophthora cinnamomi, Rhizopus oryzae, Sclerotinia sclerotiorum, Thanatephorus cucumeris* and *Verticillium dahliae*; insects belonging to the family Aphididae, as well as insects belonging to the species commonly referred to as whitefly; and/or nematodes such as species of *Meloidogyne, Heterodera, Globodera, Pratylenchus, Paratylenchus, Ratylenchus, Xiphinema, Trichodorus*, for example, and generally all parasitic plant nematodes.

Biological control or biocontrol is defined in the present invention as a method of controlling pests, diseases and undergrowth consisting of using living organisms for the purpose of controlling populations of another organism (phytopathogenic organisms).

In a particular embodiment, the invention relates to bacteria belonging to the strain with deposit number CECT8661, deposited on 23 Apr. 2014 by the Universidad de Granada in the Colección Española de Cultivos Tipo (CECT—Spanish Type Culture Collection). Throughout the present specification, reference may be made to this strain using the term "strain XT1".

In another particular embodiment, the invention relates to bacteria belonging to the strain with deposit number CECT8662, deposited on 23 Apr. 2014 by the Universidad de Granada in the Colección Española de Cultivos Tipo (CECT—Spanish Type Culture Collection). Throughout the present specification reference may be made to this strain using the term "strain XT2".

One object of the present invention relates to the use of the bacteria belonging to strains XT1 and/or XT2 in a method for the biological control of phytopathogenic organisms and/or in a method for stimulating plant growth.

Strains XT1 and XT2 belong to the species *Bacillus methylotrophicus*. This species was described by Madhaiyan et al. in 2010. It was isolated from the rhizosphere of a rice plant (*Oryza sativa*). From a phylogenetic perspective, the species *Bacillus methylotrophicus* is very closely related to *Bacillus subtilis, B. licheniformis, B. licheniformis* and *B. amyloliquefaciens*, all of which are microorganisms with various applications in the field of agriculture. The percentage of identity with these species ranges between 98.2 and 99.2%. Strains XT1 and XT2 have 99.5% and 99.3%, respectively, identity with the type species of *B. methylotrophicus*. This conclusion was reached after sequencing the whole RNAr 16S gene (1500 pb).

The scientific classification of strains XT1 and XT2 of the present invention is the following: Domain: Bacterium/Phylum: Firmicutes/Class: Bacilli/Order: Bacillales/Family: Bacillaceae/Genus: *Bacillus*.

Both strains are sporulated Gram positive bacilli. Their size ranges between 1.5 and 3.5 μm in length by 0.5 μm in width. They generate ivory-colored colonies of with irregular edges. They are oxidase negative and catalase positive.

Strains XT1 and XT2 have peritrichous flagella giving them high mobility. They generate biofilms or films that allow being adhered to animate and inanimate substrates and act as a protection factor against predators existing in the environment. Biofilm formation makes adherence of the microorganism easier; if it is administered by drip irrigation, it will adhere to the roots. If it is administered by foliar application, it will remain in the phyllosphere. Furthermore, biofilm formation both in the roots and in the leaves and stem protects the plant from being attacked by other living beings.

Accordingly, both the presence of flagella and biofilm formation entail an advantage of these bacteria (XT1 and XT2) for colonizing the habitat.

Strains XT1 and XT2 generate ellipsoidal non-deforming spores. In the 2×SG medium, these bacteria produce more than $5 \times 10^8$ spores/ml between three and five days. They are halotolerant and optimally grow in a wide range of salt concentrations [between 0 and 12% (w/v)]. They optimally grow between 20-45° C. and at a pH of 5-10. They have scarce nutritional requirements: they can grow with a wide range of organic compounds as the sole carbon source, such as citrate or sucrose. They are capable of growing with ammonium nitrate as the sole nitrogen source, without requiring the presence of yeast extract or a complex nitrogen source.

Spore formation, which allows the bacterium to remain in the habitat in adverse conditions, and the scarce nutritional requirements which allow preparing a low-cost culture medium, make strains XT1 and XT2 very appealing from the industrial viewpoint.

Strains XT1 and XT2 are facultative anaerobes. They breathe aerobically in the presence of oxygen, and in the absence thereof, for example in the roots and near the roots, they perform butanediol fermentation, producing 2,3 butanediol and acetoin. They use a number of sugars as a carbon source and energy, producing acids from said sugars. Included among the sugars these strains use are glycerol, glucose, fructose, mannitol, sorbitol, cellobiose, lactose and sucrose. It can also perform nitrogen fixation, i.e. in the absence of a nitrogen source they take up gaseous nitrogen and transform it into ammonium, which is the nitrogen source that can be used by plants. They produce dihydroxyacetone and $H_2S$.

Strains XT1 and XT2 are capable of synthesizing chelating compounds, such as siderophore compounds, which take up $Fe^{3+}$ and turn it into $Fe^{2+}$. The iron ion $Fe^{3+}$ has very little solubility at neutral pH and hence cannot be used by the organisms. Siderophores dissolve these ions into $Fe^{2+}$ complexes, which can be assimilated by mechanisms of active transport.

Strains XT1 and XT2 are capable of producing a number of extracellular enzymes with high hydrolytic capacity, which facilitate the availability of substrates for plants. Among other effects, strains XT1 and XT2 are capable of producing amylases hydrolyzing starch, urease hydrolyzing urea generating ammonium, proteases hydrolyzing gelatin and casein, lipases hydrolyzing Tween 80 and lecithin, DNases hydrolyzing DNA, phosphatases hydrolyzing organic phosphate and inorganic phosphate and ACC deaminase.

Strains XT1 and XT2 produce in CAS medium, used for detecting siderophores, a larger clearance zone (7 and 5 mm, respectively) than the *Bacillus velezensis* strain of Botrybel used as a control and producing 3 mm. Both strains grow better than the control strain (a larger amount of bacterial mass is observed on the surface of the solid medium) in solid media nitrogen-free, indicating greater nitrogen fixing activity. Therefore, their activity as a fertilizer microbial is greater.

Strains XT1 and XT2 are capable of biofilm formation. This activity has not been determined in the previous commercial preparation. This capacity allows the bacteria to more readily adhere to the roots or leaves of plants to exert their plant protection or growth stimulating action.

More specifically, it has been found that strains XT1 and/or XT2 object of the present invention have greater enzyme activity than the strain of the Botrybel preparation, produce larger halos of starch hydrolysis (amylase activity, see FIG. 3), gelatin and casein (protease activity), Tween 80 and lecithin (lipase activity), and greater ACC deaminase and phosphatase activity, determined using phenolphthalein phosphate and calcium phosphate. Hydrolysis halos are observed as the occurrence of a transparent zone in the case of starch, casein and lecithin hydrolysis; for gelatin, it can be observed that liquefaction thereof occurs, i.e., it transitions from a solid to liquid state; in the case of Tween 80, there is a more opaque precipitation zone; for ACC deaminase activity growth is studied in media with aminocyclopropane carboxylic acid as the sole nitrogen source; and finally, phosphatase activity is observed along with a pink color upon adding ammonia to the plate with phenolphthalein phosphate, and calcium phosphate solubilization is analyzed seeing the transparent zone generated around the bacterial mass grown in a medium with this compound. The activities have been analyzed using as a control the *Bacillus velezensis* strain of the Botrybel preparation.

As for activities as biological control agents against fungi, have been determined the inhibition values of strains XT1 and XT2 and the type strain of *B. methylothrophicus* against *Alternaria alternata, Aspergillus niger, Botrytis cynerea, Fusarium oxysporum, Phytophthora cactorum Phytophthora cinnamomi, Rhizopus oryzae, Sclerotinia sclerotiorum, Thanatephorus cucumeris* and *Verticillium dahliae*. The growth inhibition values are very significant in the case of *Botrytis* cinnerea. Activity was lower against *Fusarium oxysporum*. Generally, the *Bacillus* strain of Botrybel has lower (and in some cases similar) activity with respect to strains XT1 and XT2 and the type strain (see Table 1 in Example 2 below).

Strain XT1 and *B. methylothrophicus* type strain also show activity against phytopathogenic bacteria such as *Agrobacterium tumefaciens, Pectobacterium atrosepticum, Ralstonia solanacearum* and *Xanthomonas campestris*, whereas strain XT2 shows activity against *P. atrosepticum* and *X. campestris* (see Table 2 in the example 3 below).

Strains XT1, XT2 and *B. methylothrophicus* type strain show activity against *Rhopalosiphum padi* (see Table 3) and strain XT1 against whitefly (see Example 6, b1, below).

Strains XT1, XT2 and *B. methylothrophicus* type strain considerably reduce the multiplication factor of *Meloidogyne javanica* and the number of nematodes per tomato plant and the number of nematodes per g of root (see FIGS. 3, 4 and 5); likewise, treatment with strain XT1 recovered Dutch cucumber plants cultivated in greenhouse and highly infected by nematodes (see Example 4b below)

Another advantage of strains XT1 and XT2 is their high sensitivity to antimicrobial agents generally used in therapy. They are sensitive to nalidixic acid (30 μg), amoxicillin (2 μg), amoxicillin-clavulanic acid (30 μg), cefalotin (30 μg), colistin (10 μg), doxycycline 30 μg, erythromycin (15 μg), kanamycin (30 μg), nitrofurantoin (300 μg), norfloxacin (5 μg), novobiocin (30 μg), rifampicin (30 μg), trimethoprim sulfamethoxazole (1.25 μg-23.75 μg) and vancomycin (30 μg) following the diffusion in solid medium technique (Bauer and Kirby 1966). Therefore, they cannot transfer resistance genes to other microbial populations of the rhizosphere.

Strains XT1, XT2 and *B. methylotrophicus* type strain have an additional advantage against fungi used for biological control and as plant growth stimulants, which is how easy they are to culture and therefore how easy it is to reach an industrial level. The advantage against other bacterial strains of other genera described for the same purpose is the presence of spores on the part of strains XT1 and XT2, which entails total product stability during storage and in the environment when conditions are not suitable for handling said microorganisms.

Strains XT1 and XT2 and the *B. methylotrophicus* type strain produce compounds which reduce the pH, such as 2,3 butanediol and acetoin when they ferment sugars in anaerobic conditions. Furthermore, they are capable of fixing nitrogen, producing siderophores and hydrolytic enzymes. All these characteristics are mechanisms of direct plant growth stimulation (Sessitsch et al., 2002; Perrine et al., 2004; Rodriguez and Fraga, 1999; Carson et al. 2000; Essalmani and Lahlou, 2003; Choudhary and John 2009).

Strains XT1 and XT2 and type strain produce different lipopeptides, surfactants. Included among these surfactants lipopeptides are surfactin, which is similar to that produced by *Bacillus subtilis*. More specifically, the surfactin produced by strain XT1 does not have 12 carbon (12C) fatty acids in its lipid chain.

After extracting the lipopeptides following the method of Cooper et al. 1981, a yield of 0.12 g/l and 0.10 g/l of culture was obtained for strains XT1 and XT2, respectively. The type strain produced 0.6 g/l. Lipopeptide production has not been described in the case of the *Bacillus* strain of the commercial preparation Botrybel. More specifically, in addition to surfactin, strain XT1 object of the present invention produces other surfactant lipopeptides such as fengycin and lichenysin.

The cellular dry weight (CDW) of strains XT1, XT2 and of type strain is 2.7 g/l, 2.5 g/l and 2.9 g/l, respectively. In the case of strain XT1, the critical micelle concentration (CMC) is 0.0025% (0.025 mg/ml); a surface tension of 29.7 mN/m was obtained with this value. In the case of the surfactin produced by B. subtilis and marketed by Sigma®, values of 26.7 mN/m at the same CMC were obtained. In other words, strain XT1 produces very active lipopeptides surfactants showing activity similar to the surfactin available on the market.

Many lipopeptides produced by species of Bacillus show antibiotic activity, acting at the cellular membrane level in fungi and Gram negative bacteria, such as, for example, fengycins, mycobacillins, iturines, bacillomycins, surfactins, mycosubtilins, fungistatins (Volpon et al., 2000; Yilmaz et al. 2006).

More specifically, the lipopeptides produced by strain XT1 are a mixture of 13, 14 and 15 carbon atoms fatty acids which are bound to a cyclic peptide by leucine or isoleucine. The relative proportion of these fatty acids is 1, 6.5 and 5.7, respectively.

The production of enzymes (glucanases, proteases, lipases, phosphatases and urease) together with the different lipopeptides, and the release of $SH_2$ are, according to the literature (see prior art), responsible for the action of said strains in the biological control of fungi, bacteria, insects and nematodes.

Another object of the present invention relates to a method for the biological control of phytopathogenic organisms comprising the steps of:
a. obtaining the bacteria, bacteria cultures or compositions according to the present invention; and
b. putting a plant in contact with the bacteria, bacteria cultures or compositions obtained in step a).

Another object of the present invention relates to a method for stimulating plant growth and/or for the biological control of phytopathogenic nematodes (such as the species of the genera Meloidogyne, Heterodera, Globodera, Pratylenchus, Paratylenchus, Ratylenchus, Xiphinema, Trichodorus, for example, and generally all parasitic plant nematodes) comprising the steps of:
a. obtaining the bacteria, bacteria cultures or compositions according to the present invention; and
putting a plant affected by a phytopathogen in contact with the bacteria, bacteria cultures or compositions obtained in step a.

Another object of the present invention relates to a method for stimulating plant growth in plants (preferably not affected by phytopathogenic organisms) comprising the steps of:
a. obtaining the bacteria, bacteria cultures or compositions according to the present invention; and
b. putting a plant preferably not affected by a phytopathogen in contact with the bacteria, bacteria cultures or compositions obtained in step a.

Another object of the present invention relates to a method for stimulating plant growth comprising the steps of:
a. obtaining the bacteria, bacteria cultures or compositions according to the present invention; and
b. putting a plant affected by a phytopathogen in contact with the bacteria, bacteria cultures or compositions obtained in step a.

One object of the present invention relates to a method for the biological control of phytopathogenic insects belonging to the family Aphididae, as well as insects belonging to the species commonly referred to as whitefly, comprising the steps of:
a. obtaining the bacteria, bacteria cultures or compositions as previously described; and
b. putting a plant affected by a phytopathogen in contact with the bacteria, bacteria cultures or compositions obtained in step a).

In the methods of the present invention, the bacteria, cultures and/or composition of the present invention can be put into contact with the plant (affected) by foliar application, such as by means of spraying and/or dripping, for example, or by conventional irrigation, or by flood irrigation, etc.

The methods described in the present invention can furthermore comprise the use of a distribution system for distributing the bacteria, cultures or compositions of the present invention. For example, the methods of the present invention can comprise the use of drippers for distributing the bacteria, cultures or compositions of the present invention. For example, the methods of the present invention can comprise the use of self-compensating drippers for distributing the bacteria, cultures or compositions of the present invention. For example, the methods of the present invention can comprise the use of localized irrigation systems (such as microsprinklers, optionally with rotating or diffusing element, for example) for distributing the bacteria, cultures or compositions of the present invention. For example, the methods of the present invention can comprise the use of sprinklers for distributing the bacteria, cultures or compositions of the present invention.

The localized irrigation systems can be defined as methods of distributing fluids (water, fertilizers, or, in the case at hand, the bacteria, cultures or compositions according to the present invention) which, to maintain a suitable and constant level of the fluid distributed into the soil, applies said fluid dropwise, in a slow, localized and uniform manner in the plant root mass.

Localized irrigation systems can comprise drip, exudation and/or microsprinkling systems.

The person skilled in the art knows how localized irrigation systems work and how to use them.

A dripper according to the present invention is defined as a delivery point for the bacteria, cultures or compositions of the present invention in the vicinity of the plants to be treated. The person skilled in the art knows how a dripper works and how to use it.

Therefore, another object of the present invention relates to a method for the biological control (prevention) of phytopathogenic organisms, preferably fungi, bacteria and nematodes, comprising the steps of:

a. obtaining the bacteria, bacteria cultures or compositions according to the present invention; and
b. putting a plant in contact with bacteria, cultures or compositions obtained in step a, using to that end a distribution system for distributing the bacteria, cultures or compositions of the present invention.

According to the present invention, prevention is what action is taken beforehand to minimize a risk. The purpose of prevention according to the present invention is to prevent possible damage (infection by phytopathogenic organisms) from occurring.

Therefore, another object of the present invention relates to a method for the biological control (treatment) of phytopathogenic organisms, preferably fungi, bacteria, insects and nematodes, comprising the steps of:

a. obtaining the bacteria, bacteria cultures or compositions according to the present invention; and
b. putting a plant affected by a phytopathogen in contact with the bacteria, cultures or compositions obtained in step a, using to that end a distribution system for distributing the bacteria, cultures or compositions of the present invention.

In the context of the present invention, the term "treatment" is understood as the set of means the purpose of which is to cure or alleviate (palliate) diseases or symptoms.

Therefore, another object of the present invention relates to a method for the biological control of phytopathogenic organisms, preferably fungi (except the belonging to the species *Magnaporthe oryzae*), bacteria (preferably *Agrobacterium tumefaciens, Pectobacterium atrosepticum, Ralstonia solanacearum* and *Xanthomonas campestris*, insects (preferably phytopathogenic insects belonging to the family Aphididae, as well as insects belonging to the species commonly referred to as whitefly), and/or nematodes (such as the species belonging to the genera *Meloidogyne, Heterodera, Globodera, Pratylenchus, Paratylenchus, Ratylenchus, Xiphinema, Trichodorus*, and generally all parasitic plant nematodes, for example), comprising the steps of:
a. obtaining the bacteria, bacteria cultures or compositions according to the present invention; and
b. putting a plant affected by a phytopathogen in contact with the bacteria, cultures or compositions obtained in step a, using to that end a distribution system for distributing the bacteria, cultures or compositions of the present invention.

Another object of the present invention relates to a method for the biological control of phytopathogenic organisms, preferably fungi belonging to the species *Alternaria alternata, Aspergillus niger, Botrytis cynerea, Fusarium oxysporum, Phytophthora cactorum Phytophthora cinnamomi, Rhizopus oryzae, Sclerotinia sclerotiorum, Thanatephorus cucumeris* and *Verticillium dahliae*, bacteria, preferably belonging to the species *Agrobacterium tumefaciens, Pectobacterium atrosepticum, Ralstonia solanacearum* and *Xanthomonas campestris*, and/or nematodes, such as the species of the genera *Meloidogyne, Heterodera, Globodera, Pratylenchus, Paratylenchus, Ratylenchus, Xiphinema, Trichodorus*, for example, and generally all parasitic plant nematodes, comprising the steps of:
a. obtaining the bacteria, bacteria cultures or compositions according to the present invention; and
b. putting a plant affected by a phytopathogen in contact with bacteria, cultures or compositions obtained in step a, using to that end a distribution system for distributing the bacteria, cultures or compositions of the present invention.

The distribution systems for distributing the bacteria, cultures or compositions of the present invention can comprise localized irrigation systems, drippers, self-compensating drippers, microsprinklers, and/or sprinklers.

Furthermore, in the method of the present invention, the bacteria, cultures and/or compositions of the present invention can be put into contact with the affected plant at least once, preferably at least twice, preferably at least three times, preferably at least four times, preferably at least five times, preferably at least six times, or more.

Furthermore, the time interval between one application of the bacteria, culture and/or composition of the present invention and the next (if they are put in contact or applied more than once) is 2 days, or 3 days, or 5 days, or 10 days, or 15 days, or 20 days, or 30 days.

Preferably the bacteria, culture and/or composition of the present invention are put in contact with the affected plant twice, once at time (t)=0 and again after 30 days.

Preferably the bacteria, culture and/or composition of the present invention are put in contact with the affected plant once every 10 days, for 60 days, or once a day for 8-12 days.

Furthermore, in the method of the present invention, the culture and/or composition of the present invention having a microorganism concentration of at least $10^8$ colony forming units (CFU) per ml are used at a dilution between 0.5-5%. (v/v), such as 0.5%, 1%, 1.5%, 2%, 3% and/or 5% (v/v), for example. Preferably in the method of the present invention, the culture and/or composition of the present invention have a microorganism concentration of 1.5% (v/v) of a preparation containing $5\times10^8$ CFU/ml.

Therefore, one object of the present invention relates to a method for the biological control of phytopathogenic organisms, preferably fungi belonging to the species *Alternaria alternata, Aspergillus niger, Botrytis cynerea, Fusarium oxysporum, Phytophthora cactorum Phytophthora cinnamomi, Rhizopus oryzae, Sclerotinia sclerotiorum, Thanatephorus cucumeris* and *Verticillium dahliae*; bacteria, preferably belonging to the species *Agrobacterium tumefaciens, Pectobacterium atrosepticum, Ralstonia solanacearum* and *Xanthomonas campestris* and/or nematodes, such as the species of the genera *Meloidogyne, Heterodera, Globodera, Pratylenchus, Paratylenchus, Ratylenchus, Xiphinema, Trichodorus*, for example; insects belonging to the family Aphididae, as well as insects belonging to the species commonly referred to as whitefly, and generally all parasitic plant nematodes and insects, preferably whitefly, aphid, comprising the steps of:
a. obtaining the bacteria, bacteria cultures or compositions according to the present invention; and
b. putting a plant affected by a phytopathogen in contact with bacteria, cultures or compositions obtained in step a by means of distribution systems, and/or drippers, and/or localized irrigation systems, and/or sprinklers, for example, at least once, preferably at least twice, preferably at least three times, preferably at least four times, preferably at least five times, preferably at least six times, or more, using to that end a distribution system for distributing the bacteria, cultures or compositions of the present invention, where the cultures or compositions have a microorganism concentration of at least $10^8$ colony forming units (CFU) per ml, used at a dilution between 0.5-5%.(v/v), such as 0.5%, 1%, 1.5%, 2%, 3% and/or 5% (v/v), for example, preferably once every 10 days, for 60 days, or once a day for 8-12 days.

Therefore, one object of the present invention relates to a method for the biological control of phytopathogenic organisms, preferably fungi belonging to the species *Alternaria alternata, Aspergillus niger, Botrytis cynerea, Fusarium oxysporum, Phytophthora cactorum Phytophthora cinnamomi, Rhizopus oryzae, Sclerotinia sclerotiorum, Thanatephorus cucumeris* and *Verticillium dahliae* comprising the steps of:

a. obtaining the bacteria, bacteria cultures or compositions according to the present invention; and
b. putting a plant affected by a phytopathogen in contact with bacteria, cultures or compositions obtained in step a by means of distribution systems, and/or drippers, and/or localized irrigation systems, and/or sprinklers, for example, at least once, preferably at least twice, preferably at least three times, preferably at least four times, preferably at least five times, preferably at least six times, or more, using to that end a distribution system for distributing the bacteria, cultures or compositions of the present invention, where the cultures or compositions have a microorganism concentration of at least $10^8$ colony forming units (CFU) per ml, used at a dilution between 0.5-5%.(v/v), such as 0.5%, 1%, 1.5%, 2%, 3% and/or 5% (v/v), for example, preferably once every 10 days, for 60 days, or once a day for 8-12 days.

Therefore, one object of the present invention relates to a method for the biological control of phytopathogenic organisms, preferably bacteria, preferably belonging to the species *Agrobacterium tumefaciens, Pectobacterium atrosepticum, Ralstonia solanacearum* and *Xanthomonas campestris* comprising the steps of:
a. obtaining the bacteria, bacteria cultures or compositions according to the present invention; and
b. putting a plant affected by a phytopathogen in contact with bacteria, cultures or compositions obtained in step a by means of distribution systems, and/or drippers, and/or localized irrigation systems, and/or sprinklers, for example, at least once, preferably at least twice, preferably at least three times, preferably at least four times, preferably at least five times, preferably at least six times, or more, using to that end a distribution system for distributing the bacteria, cultures or compositions of the present invention, where the cultures or compositions have a microorganism concentration of at least $10^8$ colony forming units (CFU) per ml, used at a dilution between 0.5-5%. (v/v), such as 0.5%, 1%, 1.5%, 2%, 3% and/or 5% (v/v), for example, preferably once every 10 days, for 60 days, or once a day for 8-12 days.

Therefore, one object of the present invention relates to a method for the biological control of phytopathogenic organisms, preferably nematodes, such as the species of the genera *Meloidogyne, Heterodera, Globodera, Pratylenchus, Paratylenchus, Ratylenchus, Xiphinema, Trichodorus*, for example, and generally all parasitic plant nematodes, comprising the steps of:
a. obtaining the bacteria, bacteria cultures or compositions according to the present invention; and
b. putting a plant affected by a phytopathogen in contact with bacteria, cultures or compositions obtained in step a by means of distribution systems, and/or drippers, and/or localized irrigation systems, and/or sprinklers, for example, at least once, preferably at least twice, preferably at least three times, preferably at least four times, preferably at least five times, preferably at least six times, or more, using to that end a distribution system for distributing the bacteria, cultures or compositions of the present invention, where the cultures or compositions have a microorganism concentration of at least $10^8$ colony forming units (CFU) per ml, used at a dilution between 0.5-5%.(v/v), such as 0.5%, 1%, 1.5%, 2%, 3% and/or 5% (v/v), for example, preferably once every 10 days, for 60 days, or once a day for 8-12 days.

Therefore, one object of the present invention relates to a method for the biological control of phytopathogenic organisms, preferably insects, such as the species belonging to the family Aphididae, for example, as well as insects belonging to the species commonly referred to as whitefly, comprising the steps of:
a. obtaining the bacteria, bacteria cultures or compositions according to the present invention; and
b. putting a plant affected by a phytopathogen in contact with bacteria, cultures or compositions obtained in step a by means of distribution systems, and/or drippers, and/or localized irrigation systems, and/or sprinklers, for example, at least once, preferably at least twice, preferably at least three times, preferably at least four times, preferably at least five times, preferably at least six times, or more, using to that end a distribution system for distributing the bacteria, cultures or compositions of the present invention, where the cultures or compositions have a microorganism concentration of at least $10^8$ colony forming units (CFU) per ml, used at a dilution between 0.5-5%. (v/v), such as 0.5%, 1%, 1.5%, 2%, 3% and/or 5% (v/v), for example, preferably once every 10 days, for 60 days, or once a day for 8-12 days.

Therefore, one object of the present invention relates to a method for stimulating plant growth comprising the steps of:
a. obtaining the bacteria, bacteria cultures or compositions according to the present invention; and
b. putting a plant (which may or may not be affected by a phytopathogen) in contact with bacteria, cultures or compositions obtained in step a by means of distribution systems, and/or drippers, and/or localized irrigation systems, and/or sprinklers, for example, at least once, preferably at least twice, preferably at least three times, preferably at least four times, preferably at least five times, preferably at least six times, or more, using to that end a distribution system for distributing the bacteria, cultures or compositions of the present invention, where the cultures or compositions have a microorganism concentration of at least $10^8$ colony forming units (CFU) per ml, used at a dilution between 0.5-5%.(v/v), such as 0.5%, 1%, 1.5%, 2%, 3% and/or 5% (v/v), for example, preferably once every 10 days, for 60 days, once a day for 8-12 days, or twice in a period of 30 days (once at time 0 days and again at time 30 days).

Throughout the description and the claims the word "comprises" and its variants do not intend to exclude other technical features, additives, components or steps. The term "comprises" also encompasses the term "consists of". For those skilled in the art, other objects, advantages and features of the invention will be inferred in part from the description and in part from putting the invention into practice. The following examples are provided by way of illustration and do not intend to limit the present invention.

EXAMPLES

Example 1

Isolation of Strains XT1 and XT2

Strain XT1 (deposit number CECT8661), object of the invention was isolated in 1999 from a sample from the rhizosphere of a soil close to Lake Capacete, located in Fuente de Piedra, Malaga (Spain). Strain XT2 (deposit number CECT8662) was isolated in 2010 in a soil close to the mouth of the Velez River (Malaga, Spain). The medium used was MY medium (Moraine and Rogovin 1966) added with 7.5% sea salts in the case of strain XT1 and the MY medium with 3% sea salts in the case of strain XT2. Both strains were selected for their characteristics of about 5000 colonies (searching for those with higher surfactant activity by means of the method of Jain et al. 1991).

Example 2

Use of Strains XT1, XT2 and Type Strain as Antifungal Agents

Activity against fungi (Table 1) was established by seeding strains XT1, XT2, the type strain and the Botrybel strain in a small area in PDA medium (potato dextrose agar). Then was placed at the end opposite a piece of agar of about 1 $cm^2$ with mycelium of the fungus to be tested, and after 20 days and after incubation at 25° C., the maximum and minimum radius of the mycelium of the fungus was measured to calculate the percentage of growth reduction of the fungus

TABLE 1

Maximum and minimum inhibition values against different fungi expressed in mm, in parenthesis percentage of reduction of the mycelium.

| Fungi | Antifungal activity | | | |
|---|---|---|---|---|
| | XT1 | XT2 | Type strain | Botrybel |
| *Alternaria alternata* | 27 and 14 (49) | 24 and 19 (21) | 25 and 8 (68) | 24 and 20 (17) |
| *Aspergillus niger* | 30 and 22 (27) | 25 and 10 (60) | ND | 0 |
| *Botrytis cynerea* | 45 and 8 (83) | 45 and 2 (96) | 40 and 20 (50) | 46 and 16 (56) |
| *Fusarium oxysporum* | 30 and 28 (7) | 0 | 32/29 (10) | 0 |
| *Phytophthora cactorum* | 8 and 3 (63) | 8 and 3 (63) | ND | 8 and 6 (21) |
| *Phytophthora cinnamomi* | 22 and 16 (28) | 22 and 15 (32) | 16 and 12 (21) | 20 and 14 (30) |
| *Rhizopus oryzae* | 45 and 8 (82) | 50 and 12 (76) | ND | 40 and 7 (82) |
| *Sclerotinia sclerotiorum* | 16 and 7 (56) | 16 and 12 (25) | 16 and 10 (37) | ND |
| *Thanatephorus cucumeris* | 12 and 7 (42) | 16 and 10 (37) | 16 and 7 (56) | ND |
| *Verticillium dahliae* | 25 and 12 (52) | 24 and 12 (50) | 25 and 14 (44) | 23 and 13 (44) |

ND: Not determined

Among the tested fungi, the highest inhibition was achieved against *Botrytis* (strains XT1 and XT2) and the lowest inhibition was achieved against *Fusarium* (FIG. 1).

The antimicrobial activity of strains XT1 and XT2 and the type strain against *Saccharomyces cerevisiae* (a beneficial yeast with enormous industrial applications) was also determined and the absence thereof was observed, i.e., the inhibition zone was zero mm.

Example 3

Use of Strains XT1, XT2 and Type Strain as Antibacterial Agents

Figure 2:
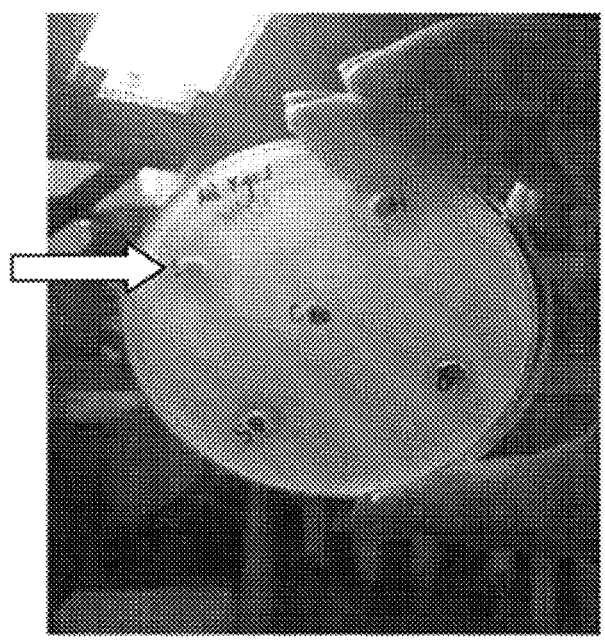
FIG. 2. Activity of strain XT1 against *Agrobacterium tumefaciens*

The antibacterial activity was determined by incorporating, in a Petri dish with trypticase soybean agar (TSA), an overlay with 6 ml of sterile TSA at 45° C. and 1 ml of a culture of the phytopathogenic strain to be analyzed in exponential growth phase at a concentration equivalent to 1 on the Mac Farland scale. Then once the medium solidified, it was inoculated in a well 100 µl of supernatant from the cultures. After 24 hours of incubation, the inhibition zone was measured (Table 2. FIG. 2).

TABLE 2

Antibacterial activity. Results expressed in mm of growth inhibition.

| | X. campestris | P. atrosepticum | R. solanacearum | A. tumefaciens |
|---|---|---|---|---|
| XT1 | 6 | 3 | 1 | 4 |
| XT2 | 5 | 2 | R | R |
| Type strain | 8 | 5 | 3 | 5 |

R: Resistant

Example 4

Figure 3:
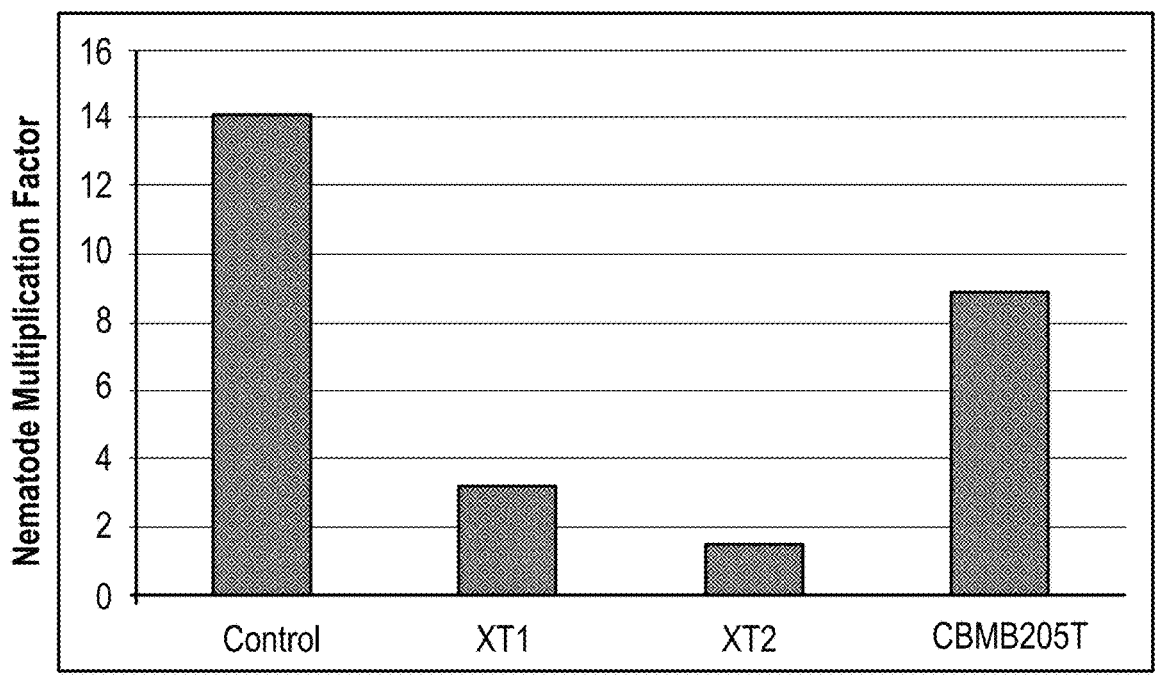
FIG. 3. Multiplication factor of *M. javanica* in tomato plants treated with strains XT1, XT2 and type strain.
Figure 4:
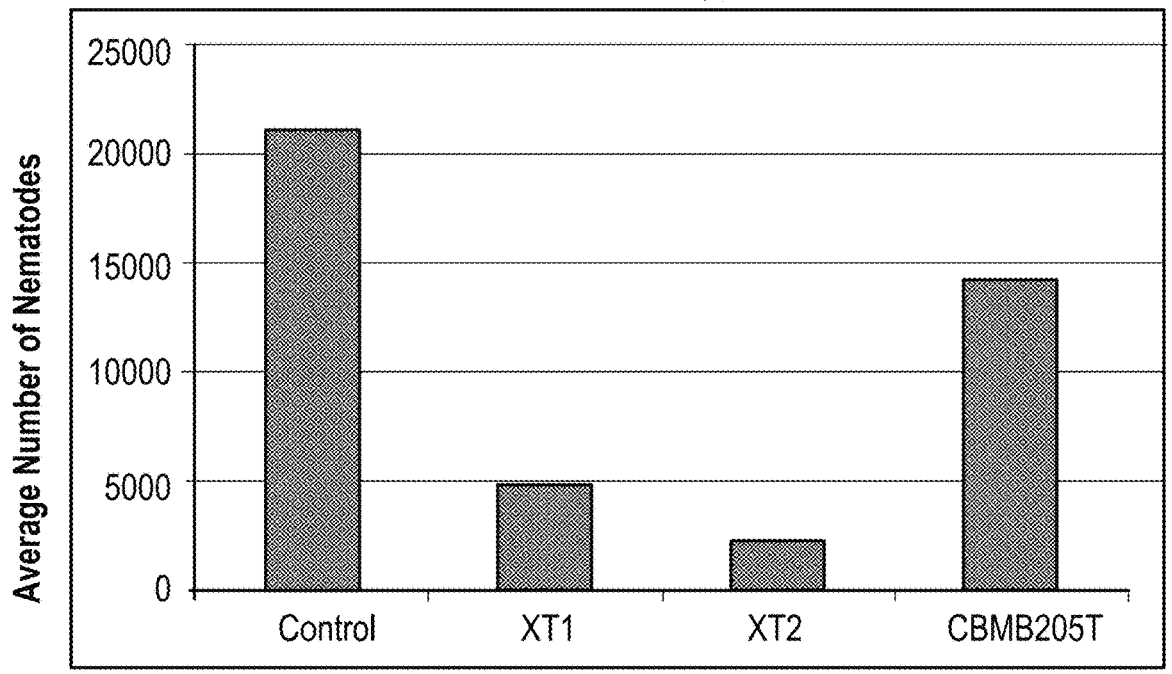
FIG. 4. Average number of nematodes found per plant treated with strains XT1, XT2 and type strain.
Figure 5:
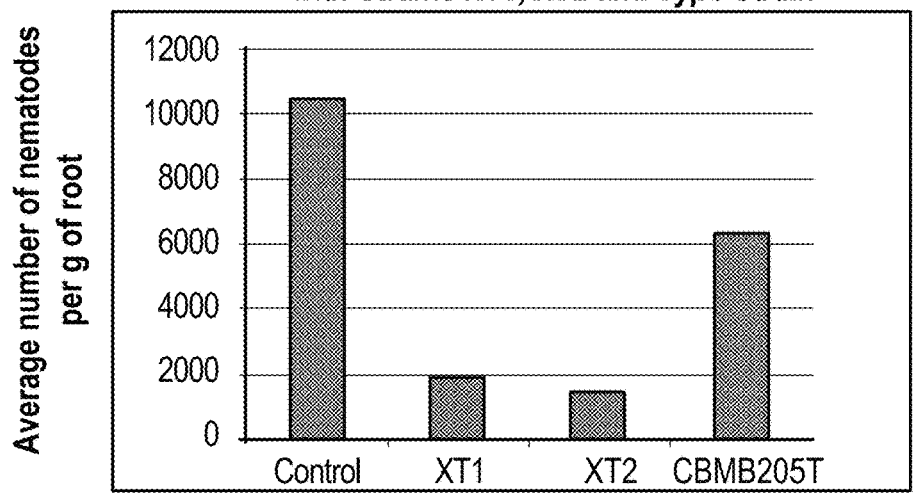
FIG. 5. Average number of nematodes per g of root found in plants treated with strains XT1, XT2 and type strain.

Use of Strains XT1, XT2 and Type Strain as Agents for Biological Control of Nematodes a) Tests in tomato plants inoculated with *Meloidogyne javanica* (FIGS. 3, 4, and 5)

Five batches of 10 tomato plants (*Solanum lycopersicum*) each were used. Three batches were inoculated with the selected strains ($2 \times 10^8$ CFU) and then with *M. javanica* J2 (1500). Finally, two batches, with and without nematodes, were used as control. After 50 days the number of nematodes in the soil of each plant and in the roots was determined, and the multiplication factor (Talavera et al. 2012) was calculated. The obtained results can be seen in FIGS. 3, 4 and 5.

It is observed that all the strains reduce the nematode multiplication factor, the number of nematodes per plant and the number of nematodes per g of root, the reductions being more pronounced in the case of strains XT1 and XT2.

b) Greenhouse test with strain XT1 in a Dutch cucumber crop with recurrent problems every year due to excess moisture in the soil, difficulty in rooting and a high incidence of rot in the root, as well as infection by nematodes.

A sector of 2000 m² was used for injection in the drip irrigation and another sector similar was used as a control. 7.5 l of culture were applied in 6 applications separated by a period of 10 days (1, 250 l of a culture with at least $10^8$ CFU/ml in each application). Both in the control sector and in the treatment sector the usual fertilizing and plant health treatments were maintained. The number of plants lost during this treatment in the control sector was 36, whereas that for the plants treated with strain XT1 was 6. The differences in production were also significant, a 30% higher production being obtained in the treated sector.

Example 5

Use of Strain XT1, XT2 and Type Strain as Agents for Biological Control of Insects a) Laboratory experiments were conducted with barley aphid (*Rhopalosiphum padi*) and *Anthocoris nemoralis* for the purpose of determining the mortality percentage, generating the bacterial cultures of the three strains of *B. methylotrophicus* and the surfactants thereof, on these insects. Given that the first is a sucking insect, the tests are only conducted topically, whereas in the second case they are conducted both topically and by ingestion.

The activity of the bacterial cultures of strains XT1 and XT2 with $5 \times 10^8$ CFU/ml, and of their surfactants at a concentration 1/1000 in distilled water, in both types of insects, were analyzed by topical use. Ten individuals were used for each treatment. In the case of *Anthocoris*, 5 µl were applied with a pipette on the body thereof and the aphids were impregnated with the same amount with a brush. The bacterial culture medium SG was used as a control. The obtained results expressed in mortality percentage after 48 h are the following:

TABLE 3

Mortality by topical use in the barley aphid
*Rhopalosiphum padi* and *Anthocoris nemoralis*.
Results expressed in percentage of individuals

| Insect | XT1 | Surfactant XT1 | XT2 | Surfactant XT2 | Control (Culture medium) |
|---|---|---|---|---|---|
| *Anthocoris* | 70 | 100 | 20 | ND | 70 |
| Aphids | 30 | 60 | 80 | 60 | 10-30 |

The activity of the bacterial cultures of strains XT1, XT2 and the *B. methylotrophicus* type strain with $5 \times 10^8$ CFU/ml, and of the three corresponding surfactants, at a concentration 1/1000 in distilled water by ingestion was likewise analyzed on *Anthocoris nemoralis*. Water and Tween 80 (1/1000 dilution) was used as a control. The different products were applied on a sponge moistened with water (1 ml) and by spraying (0.25 ml) on the food (*Ephestia kuheniella* eggs) making sure it was well covered. Four repetitions of five individuals were done for each treatment, being observed daily for 6 days. The obtained results, expressed in mortality percentage, are indicated in the following table:

TABLE 4

Mortality by ingestion in *Anthocoris nemoralis*.
Results expressed in percentage of individuals.

Figure 6:
FIG. 6. Nectarine tree affected by aphids before treatment with strain XT1.

| Type strain | Surfactant Type strain | XT1 | Surfactant XT1 | XT2 | Surfactant XT2 | Control (Water) | Tween 80 |
|---|---|---|---|---|---|---|---|
| 5 | 25 | 15 | 20 | 15 | 20 | 10 | 5 | b) Furthermore, a nectarine tree *Prunus persica* var. nectarine highly affected by green and black aphids (see FIG. 6) was treated. With a culture of XT1 with $5 \times 10^8$ CFU/ml. Specifically, 50 ml of a 5% dilution of said culture was administered by foliar application every 10 days. After the second application, the population virtually disappeared although small zones still had aphids at the end of some leaves that remained rolled up and were removed by hand. After one month, the pest was controlled.

c) The disappearance of whitefly was likewise observed in a greenhouse tomato culture treated with strain XT1 (see Example 6 b1)

Example 6

Use of Strains XT1, XT2 and Type Strain as Plant Strengthening Agents a) Pot test with pepper plants (genus *Capsicum*) and pumpkin plants (genus *Cucurbita*) with strains XT1, XT2 and type strain.

Sixteen seedlings 5 cm in height coming from each of the preceding plants that were transplanted to pots 10 cm in diameter and 15 cm in height were used and were left exposed at room temperature (temperature range of 20-38° C.) for 35 days. The pots were irrigated every each 48 h with the same amount of water (about 50 ml). Four batches of 4 pots of each type of plant were made. Five ml of a 1/100 dilution of a culture of *Bacillus* strain XT1, strain XT2 and type strain with $5 \times 10^8$ CFU/ml were added every seven days to three batches of each type of plant, after irrigating. A batch of four pots of each type was used as a control and therefore it was not inoculated with bacterial cultures. After 35 days the aerial part was cut and dried. The obtained results are observed in the enclosed table.

TABLE 5

Plant strengthening effect of strains XT1, XT2, and type strain

| | Pumpkin | | Pepper | |
|---|---|---|---|---|
| | Weight (g) | Increase with respect to the control (%) | Weight (g) | Increase with respect to the control (%) |
| Type strain | 6.7 ± 1.4 | 45.6 | 5.6 ± 1.5 | 64.7 |
| XT1 | 8.15 ± 1.8 | 77.1 | 5.2 ± 1.2 | 52.9 |
| XT2 | 5.4 ± 0.4 | 17.4 | 5.2 ± 1.3 | 52.9 |
| Control | 4.6 ± 0.5 | 0 | 3.4 ± 1.4 | 0 |

Note: In the cucumber crop there was a loss, due to weather conditions and pests, of 50% of the plants, in the case of the control and in those plants irrigated with the type strain, and of 25% in the plants irrigated with strain XT2; however all the plants irrigated with XT1 were maintained in optimal conditions.

b) Furthermore, the following were conducted with strain XT1:

b.1. Test in greenhouse pear tomato crops.

Treatments were performed by foliar application at three different doses of the culture broth containing at least $10^8$ CFU/ml (0.5, 1 and 1.5% v/v) by means of spraying and with two repetitions (at time zero and after 30 days). Six plants were planted in each treatment. An untreated control was used. During the period of the study, in the greenhouse, and therefore in the control, there were several pests: whitefly, aphid, oidium and *Botrytis*. The number of plants that were lost in the zones treated with the culture of strain XT1 was less than the number lost in the control zone, the most suitable dose being the 1.5% (v/v) dose. In addition, the weight of the tomatoes picked from treated plants was greater than the weight of the control plant (see Table 6).

TABLE 6

Tomato plants lost and weight of the tomatoes picked in two
greenhouse pear tomato crop zones after treatment with XT1

| | Treatment | | | |
|---|---|---|---|---|
| Experience | 1.5% (1) | CONTROL (1) | 1.5% (2) | CONTROL (2) |
| Plants lost | 1 | 4 | 0 | 3 |
| Weight of the tomatoes (total kg) | 3.6 | 3.1 | 3.8 | 3.1 |

These results showed a clear trend between the application of the product and the increase in the production of the plants with respect to the controls that can be attributed to the stimulating effect on the plant's metabolism. Furthermore, the treated plants showed a significant reduction of the whitefly and aphid pests and recovered from infection by *Botrytis* and oidium.

b.2. Longer-term pot test with strain XT1 with healthy and already developed tomato plant (*Solanum lycopersicum*), pepper plant (genus *Capsicum*), pumpkin plant (genus *Cucurbita*) and cucumber plant (*Cucumis sativus*) crops.

Figure 7:
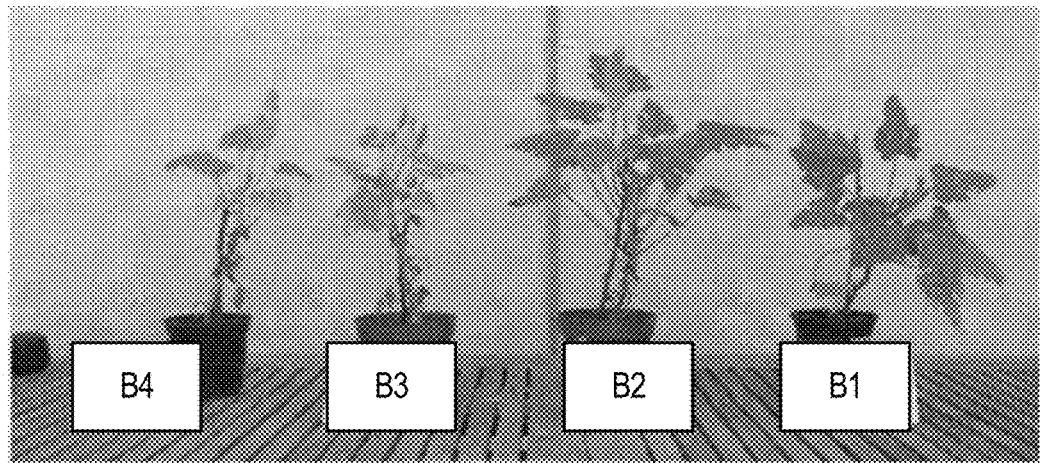
FIG. 7. Pumpkin plant growth after 50 days of cultivation in pots at room temperature. Pots B1 and B2 were inoculated with strain XT1 whereas the B3 and B4 were not inoculated so they could be used as a control.

Four seedlings 10 cm in height of each of the preceding species (tomatoes (*Solanum lycopersicum*), peppers (genus *Capsicum*), pumpkin (genus *Cucurbita*) and cucumber (*Cucumis sativus*) were used. They were transplanted to pots 10 cm in diameter and 15 cm in height and were left exposed at room temperature (temperature range of 15-32° C.). The pots were irrigated every 48 h with the same amount of water (about 100 ml). Five ml of a 1/100 dilution of a culture of *Bacillus* XT1 were added every seven days to half the pots, after irrigating. The other half wasused as a control and therefore was not inoculated. After 50 days the aerial part was cut and dried. Likewise, the number of leaves, flowers and fruits, and the height thereof, were recorded. The obtained results (mean values) are observed in the enclosed table. An increase in the aerial vegetation weight of 86%, an increase in the number of leaves of 57.6% and an increase in the number of fruits and flowers of 1 12.5 and 137.5%, respectively, are obtained (see Table 7). Furthermore, the size of the treated plant increased by 38.3%. The results in the pumpkin crop can be seen FIG. 7.

TABLE 7

Effect of irrigation with XT1 in pepper, cucumber, tomato and pumpkin plants. The mean is indicated.

| | Treatment | No. of leaves | Weight of aerial part (g) | Height (cm) | No. fruits | No. flowers |
|---|---|---|---|---|---|---|
| Pepper | None | 12 | 7.7 | 38 | 0 | 0 |
| Pepper | XT1 | 14 | 12.6 | 46.5 | 1 | 1 |
| % increase | | 16.7 | 62 | 22.4 | 100 | 100 |
| Cucumber | None | 7 | 12.1 | 30.5 | 0 | 3.5 |
| Cucumber | XT1 | 14 | 24.3 | 33 | 0.5 | 8.5 |
| % increase | | 100 | 101.2 | 8.2 | 50 | 142.9 |
| Pumpkin | None | 8 | 8.9 | 30.5 | 0 | 3.5 |
| Pumpkin | XT1 | 12.5 | 20.4 | 33.5 | 2 | 5.5 |
| % increase | | 56.2 | 128.5 | 9.8 | 200 | 57.1 |
| Tomato | None | ND | 13.2 | 46 | 0 | 0 |
| Tomato | XT1 | ND | 20.1 | 52 | 1 | 2.5 |
| % increase | | | 52.7 | 113 | 100 | 250 |
| Mean overall increase | | 57.6 | 86 | 38.3 | 112.5 | 137.5 |

The invention claimed is:

1. A method for treating a plant for the biological control of phytopathogenic nematodes comprising the step of:
   a. contacting a plant with a composition comprising: a plurality of a microorganism, a culture of the plurality of the microorganism, surfactant lipopeptides obtained from the culture of the plurality of the microorganism, or combinations thereof;
   wherein the microorganism is *Bacillus methylotrophicus* strain XT1 (deposit number CECT8661) or is a related strain having a 16S rRNA gene sequence with at least 99.7% identity to the 16S rRNA gene sequence of the *B. methylotrophicus* strain XT1; wherein
      contacting the plant with the composition results in a greater reduction of the phytopathogenic nematodes on the plant, as compared to contacting the plant with an equivalent composition having the microorganism replaced with *Bacillus methylotrophicus* type strain CBMB205T; and wherein the greater reduction in the phytopathogenic nematodes on the plant comprises at least one of: a greater reduction in the multiplication factor of the phytopathogenic nematodes, a greater reduction in the total number of phytopathogenic nematodes on the plant, or a greater reduction in the total number of phytopathogenic nematodes per gram of root of the plant.

2. The method according to claim 1, wherein the phytopathogenic nematodes belong to one of the following genera: *Meloidogyne, Heterodera, Globodera, Pratylenchus, Paratylenchus, Ratylenchus, Xiphinema* or *Trichodorus*.

3. The method according to claim 1, wherein the composition is a bacterial culture of the plurality of the microorganism.

4. The method according to claim 1, wherein the microorganism is the B. methylotrophicus strain XT1.

5. The method according to claim 1, wherein the phytopathogenic nematodes belong to the genus *Meloidogyne* or *Xiphinema*.

6. The method according to claim 1, wherein the phytopathogenic nematodes belong to the genus *Meloidogyne*.

7. The method according to claim 1, wherein the phytopathogenic nematodes are of the species *Meloidogyne javanica*.

8. The method according to claim 1, wherein the plant is a crop plant.

9. The method according to claim 1, wherein the plant is a tomato plant or a cucumber plant.

10. The method according to claim 1, wherein the plant is a tomato plant.

11. The method according to claim 1, wherein the related strain has a 16S rRNA gene sequence with at least 99.8% or at least 99.9% identity to the 16S rRNA gene sequence of the *B. methylotrophicus* strain XT1.

* * * * *